United States Patent
Inazuki

(10) Patent No.: US 9,861,598 B2
(45) Date of Patent: Jan. 9, 2018

(54) KETOPROFEN LYSINE SALT-CONTAINING AQUEOUS PATCH

(75) Inventor: Masahiro Inazuki, Naruto (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 0 days.

(21) Appl. No.: 12/934,443

(22) PCT Filed: Mar. 24, 2009

(86) PCT No.: PCT/JP2009/055848
§ 371 (c)(1),
(2), (4) Date: Apr. 13, 2011

(87) PCT Pub. No.: WO2009/119601
PCT Pub. Date: Oct. 1, 2009

(65) Prior Publication Data
US 2011/0184066 A1    Jul. 28, 2011

(30) Foreign Application Priority Data

Mar. 25, 2008  (JP) .................................. 2008-078486

(51) Int. Cl.
| | |
|---|---|
| *A61K 47/10* | (2017.01) |
| *A61K 31/192* | (2006.01) |
| *A61K 9/70* | (2006.01) |

(52) U.S. Cl.
CPC .......... *A61K 31/192* (2013.01); *A61K 9/7061* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 5,614,171 A | * | 3/1997 | Clavenna et al. ............. 424/45 |
| 5,891,920 A | | 4/1999 | Hirano et al. |

(Continued)

FOREIGN PATENT DOCUMENTS

| | | |
|---|---|---|
| EP | 1 300 143 A1 | 4/2003 |
| EP | 1987822 A1 * | 11/2008 |

(Continued)

OTHER PUBLICATIONS

Login ("Pyrrolidone-based surfactants (a literature review)". JAOCS, 1995: 72(7):759-771).*

(Continued)

*Primary Examiner* — Marcos Sznaidman
*Assistant Examiner* — Rayna B Rodriguez
(74) *Attorney, Agent, or Firm* — Crowell & Moring LLP

(57) ABSTRACT

A ketoprofen-containing aqueous patch is provided in which not only operational efficiency in producing is improved, but also the aqueous patch has excellent storage stability and transdermal absorption of ketoprofen. The ketoprofen lysine salt-containing aqueous patch includes a backing layer and an adhesive (paste) layer laminated thereon. The aqueous patch includes as a main active ingredient a ketoprofen lysine salt completely dissolved in a paste including not glycerin but a polyethylene glycol having an average molecular weight of 1000 or less. In the ketoprofen lysine salt-containing aqueous patch, the polyethylene glycol having an average molecular weight of 1000 or less is one or more polyethylene glycols selected from the group consisting of Polyethylene glycol 200, Polyethylene glycol 400, Polyethylene glycol 600, and Polyethylene glycol 1000.

4 Claims, 1 Drawing Sheet

(56) References Cited

U.S. PATENT DOCUMENTS

| | | | | |
|---|---|---|---|---|
| 6,455,067 | B1* | 9/2002 | Woo et al. | 424/449 |
| 2007/0231591 | A1* | 10/2007 | Tsuru et al. | 428/497 |

FOREIGN PATENT DOCUMENTS

| | | |
|---|---|---|
| JP | 58-83623 | 5/1983 |
| JP | 61-275212 | 12/1986 |
| JP | 5-78241 | 3/1993 |
| JP | 2001-342130 | 12/2001 |
| JP | 2002-20274 | 1/2002 |
| JP | 2002-29970 | 1/2002 |
| JP | 2002-193793 | 7/2002 |
| JP | 2006-104170 | 4/2006 |
| WO | WO 96/11022 | 4/1996 |
| WO | WO 2007/097047 A1 * | 8/2007 |

OTHER PUBLICATIONS

Gallagher et al ("Ketoprofen: release from, permeation across and rheology of simple gel formulations that simulate increasing dryness." International Journal of Pharmaceutics, 2003; 268:37-45).*

International Search Report (Form PCT/ISA/210) dated May 12, 2009 with English-language translation (4 pages).

Written Opinion of the International Searching Authority (Form PCT/ISA/237) dated May 12, 2009 with English-language translation (9 pages).

L. N. Taneja et al., "Solid Dispersions of Ketoprofen: In-Vitro Characterization and Bioavailability Assessment," Indian drugs, vol. 34, No. 2, 1997, pp. 72-77.

Maria Victoria Margarit et al., "Physical characteristics and dissolution kinetics of solid dispersions of ketoprofen and polyethylene glycol 6000," International Journal of Pharmaceutics, vol. 108, 1994, pp. 101-107.

* cited by examiner

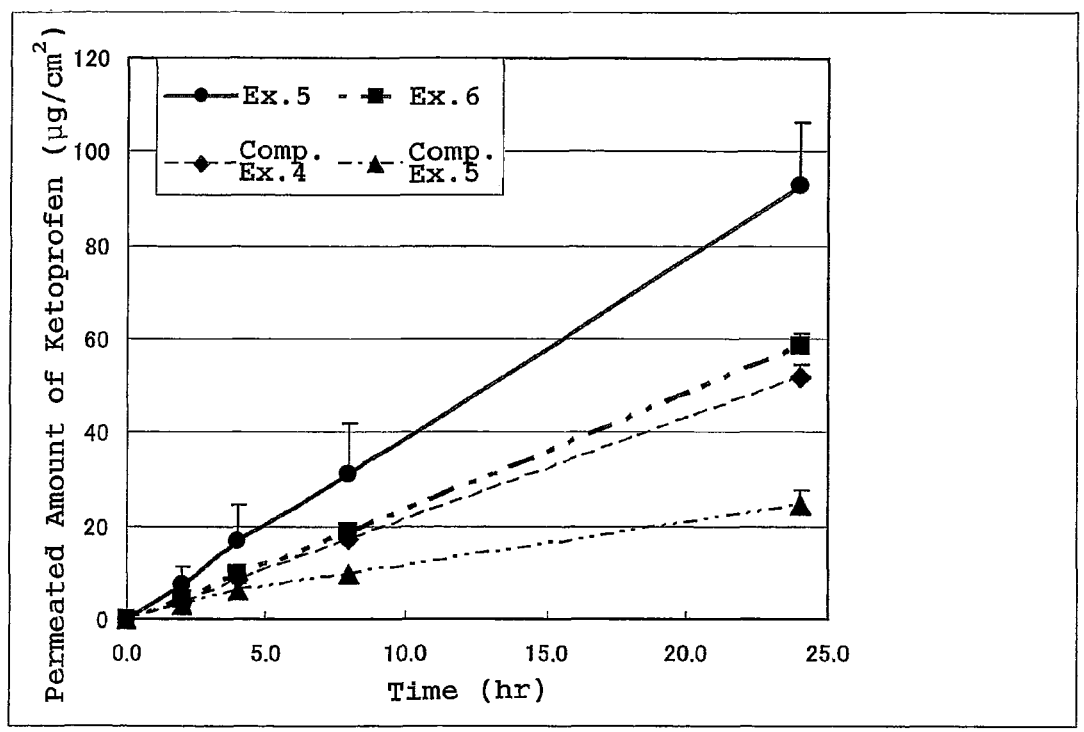

KETOPROFEN LYSINE SALT-CONTAINING AQUEOUS PATCH

TECHNICAL FIELD

The present invention relates to an aqueous patch which includes a ketoprofen lysine salt as an active ingredient, and specifically to an aqueous patch which includes a highly water-soluble ketoprofen lysine salt as an active ingredient and polyethylene glycol having an average molecular weight of 1000 or less, the polyethylene glycol serving as a paste base.

BACKGROUND ART

There are some aqueous patches which include ketoprofen, which has an anti-inflammatory activity, as an active ingredient (Patent Documents 1 and 2). However, since ketoprofen, being the active ingredient, it has low water-solubility, it is dissolved or dispersed in a paste by using a solubilizer or a dispersant when it is blended in the paste base to make an aqueous patch.

Examples of such solubilizers include particular solubilizers such as crotamiton known as a solubilizer for poorly soluble drugs, fatty acids, fatty acid esters, essential oils, polyalcohols, surfactants, and N-substituted-o-toluidine derivatives (Patent Document 3). On the other hand, in the method using a dispersant, a process including dispersing ketoprofen in a liquid dispersant and mixing it with an acidic adhesive base is used (Patent Document 4).

Such production methods had fundamental drawbacks of low operational efficiency in production, since ketoprofen itself had low water-solubility and therefore the methods required some contrivance.

Specifically, many of such particular solubilizers used for dissolving ketoprofen are generally lipophilic, and careless addition of these solubilizers to other paste components in producing aqueous patches may cause unfavorable effects on the physical properties of the patches such as insolubility of hydrophilic polymers or separation of lipophilic solvents.

Furthermore, in the case of conventional ketoprofen-containing aqueous patches which include glycerin in high concentration as a base component, they had the problem of poor transdermal absorption due to insufficient solubility of ketoprofen in the base. In addition, they also had the problem of poor storage stability, which results from the esterification reaction. In this case, the esterification reaction proceeds between carboxylic acid groups in ketoprofen molecules and hydroxyl groups in polyalcohols (for example, glycerin), lower alcohols, menthol, and the like as solubilizers at even relatively low temperatures by catalysis of weak acids which are base components for aqueous patches, such as organic acids and polyacrylic acid.

Patent Document 5 proposed stabilization of a non-steroidal antiinflammatory analgesic agent which includes ketoprofen having a carboxylic acid group in the molecule by dissolving or dispersing the agent in glycerin and glycol having 3 to 30 carbon atoms. However, there is a concern regarding long-term stability that even the conventional patches described in Patent Document 5 might lose their storage stability due to the esterification reaction, since glycerin is used as a base component when ketoprofen is blended as an active ingredient.

Furthermore, in general, when drugs are dispersed in the patch paste, transdermal absorption of the drugs themselves is reduced while their storage stability is increased. Therefore, there is a demand for a further improved patch which includes ketoprofen as an active ingredient and has both good storage stability and transdermal absorption.

[Patent Document 1] Japanese Patent Laid-Open Sho 58-083623
[Patent Document 2] Japanese Patent Laid-Open Sho 61-275212
[Patent Document 3] International Publication WO 96/11022
[Patent Document 4] Japanese Patent Laid-Open 2006-104170
[Patent Document 5] Japanese Patent Laid-Open 2002-193793

DISCLOSURE OF THE INVENTION

Problems to be Solved by the Invention

The present invention solves the above problems. It is an object of the present invention not only to improve operational efficiency in producing a ketoprofen-containing aqueous patch, but also to provide an aqueous patch which has excellent storage stability and transdermal absorption of ketoprofen.

As a result of dedicated research to solve the above problems, the inventor has found that an aqueous patch which is produced with high operational efficiency, retains transdermal absorption of ketoprofen, and has good storage stability due to absence of glycerin could be obtained by selecting as an active ingredient (effective ingredient) a ketoprofen salt or particularly a ketoprofen lysine salt, which has high water-solubility among other derivatives, and furthermore dissolving such salt in a paste which includes polyethylene glycol as a base component without using glycerin, the polyethylene glycol having an average molecular weight of 1000 or less and interacts weakly with ketoprofen, and completed the present invention.

Means for Solving the Problems

Therefore, one basic embodiment of the present invention is a ketoprofen lysine salt-containing aqueous patch which includes a backing layer and an adhesive (paste) layer laminated thereon, wherein the aqueous patch includes as an active ingredient a ketoprofen lysine salt completely dissolved in a paste including not glycerin but a polyethylene glycol having an average molecular weight of 1000 or less.

More preferably, the present invention provides the ketoprofen lysine salt-containing aqueous patch, wherein the polyethylene glycol having an average molecular weight of 1000 or less is one or more polyethylene glycols selected from the group consisting of Polyethylene glycol 200, Polyethylene glycol 400, Polyethylene glycol 600, and Polyethylene glycol 1000.

More preferably, the present invention provides the ketoprofen lysine salt-containing aqueous patch comprising 2 to 30% of the polyethylene glycol having an average molecular weight of 1000 or less. Even more preferably, the present invention provides the ketoprofen lysine salt-containing aqueous patch, wherein the paste components include 0.1 to 5% by weight of the ketoprofen lysine salt, 30 to 80% by weight of water, 2 to 30% by weight of the polyethylene glycol having an average molecular weight of 1000 or less, 3 to 20% by weight of an aqueous polymer, 10 to 30% by weight of a humectant, and 0.001 to 1% by weight of a polyvalent metal compound.

Thus, the most preferable patch of the present invention is a ketoprofen lysine salt-containing aqueous patch which includes 0.1 to 5% by weight of the ketoprofen lysine salt as an active ingredient in a paste, wherein the paste includes as paste components not glycerin but 2 to 30% by weight of the polyethylene glycol having an average molecular weight of 1000 or less, 3 to 20% by weight of an aqueous polymer, 10 to 30% by weight of a humectant, 0.001 to 1% by weight of a polyvalent metal compound, and 30 to 80% by weight of water.

Advantageous Effects of the Invention

The present invention provides an aqueous patch which is produced with a simpler manufacturing operation and includes a ketoprofen lysine salt stably by employing a highly water-soluble ketoprofen lysine salt as an active ingredient and by dissolving such a salt in a paste including as paste components not glycerin but a polyethylene glycol having an average molecular weight of 1000 or less.

The present invention made it possible to provide an aqueous patch which has both excellent transdermal absorption and storage stability of ketoprofen, which conventional aqueous patches including ketoprofen in a dissolved or dispersed form had not successfully had.

The ketoprofen lysine salt-containing aqueous patch provided by the present invention has excellent long-term storage stability even under severe conditions such as high temperatures greater than 40° C. Furthermore, the aqueous patch has excellent transdermal absorption of ketoprofen.

While the reason why such excellent effects are obtained is not necessarily clear, it is believed that the polyethylene glycol having an average molecular weight of 1000 or less used as a paste component has a higher ability to dissolve ketoprofen in free forms (molecular forms) generated in the paste when compared to formulations including a humectant such as other polyalcohols and the polyethylene glycol is unreactive to ketoprofen even in the acidic range of pH 3.5 to 6.5, thereby stabilizing ketoprofen.

In other words, it is believed that, in the present invention, ketoprofen can be blended stably in a dissolved form by mixing a ketoprofen lysine salt in an acidic adhesive base including the polyethylene glycol without using glycerin, which is generally used for aqueous patches, so that excellent storage stability is achieved.

BRIEF DESCRIPTION OF THE DRAWINGS

FIG. 1 is a graph showing the amount of ketoprofen which permeated the skin, as measured by the in vitro test in Experimental Example 2 of the present invention.

BEST MODE FOR CARRYING OUT THE INVENTION

The ketoprofen lysine salt used as an active ingredient in the aqueous patch provided by the present invention is formed by salt linkage between a carboxyl group within a ketoprofen molecule and basic lysine. Since the ketoprofen lysine salt is significantly high water-soluble as compared to ketoprofen and can dissolve directly in water, operational efficiency in production using the salt is high.

The aqueous patch provided by the present invention includes preferably 0.1 to 5.0% by weight of a ketoprofen lysine salt, and more preferably 0.3 to 3.0% by weight of the salt. In other words, the patch including less than 0.1% by weight of a ketoprofen lysine salt does not provide a sufficient medicinal effect, while the patch including more than 5.0% by weight of a ketoprofen lysine salt is unsuitable due to development of adverse effects such as skin irritation caused by overdose and diseconomy.

Preferably, in the aqueous patch provided by the present invention, water is used for dissolving a ketoprofen lysine salt. The water content is 30 to 80% by weight, and preferably 40 to 70% by weight based on the weight of the paste. When the water content is more than 80% by weight, paste viscosity is reduced, and thus shape retention is reduced and the paste becomes undesirably sticky. Furthermore, water content of more than 80% by weight is not preferable, since the adhesive power of the patch is significantly reduced and the patch does not have sufficient adhesiveness to the site onto which the patch is applied. On the other hand, when the water content is less than 30% by weight, paste viscosity is increased excessively, and handling the paste in producing patches by spreading it onto a backing layer and a liner becomes difficult. Moreover, water content of less than 30% by weight is not preferable, since excessively strong adhesive power causes pain or skin irritation when the patch is peeled off.

In the present invention, the polyethylene glycol having an average molecular weight of 1000 or less is used singly or in a combination of two or more thereof for blending a ketoprofen lysine salt as an active ingredient stably in an aqueous base.

Preferably, Polyethylene glycol 200, Polyethylene glycol 300, Polyethylene glycol 400, Polyethylene glycol 600, or Polyethylene glycol 1000 is used as the polyethylene glycol having an average molecular weight of 1000 or less. More preferably, Polyethylene glycol 300, Polyethylene glycol 400, or Polyethylene glycol 600 is used.

One feature of the present invention is that the polyethylene glycol having an average molecular weight of 1000 or less is used as a paste component instead of glycerin. Using the polyethylene glycol having an average molecular weight of more than 1000 is not preferable, since its melting point exceeds 40° C. and does not allow for sufficient dispersion of aqueous polymers to be blended as a paste component, thus resulting in problems such as an occurrence of un-dissolved lump of the polymers in the paste.

The content of the polyethylene glycol in the paste composition is preferably 2 to 30% by weight, and more preferably 5 to 20% by weight. In other words, when the content of the polyethylene glycol is less than 2% by weight, ketoprofen in free forms generated in the aqueous patch cannot be sufficiently dissolved. On the other hand, when the content of the polyethylene glycol is more than 30% by weight, for example, a problem occurs that the polyethylene glycol which the gel surface cannot retain any more rises to the surface and causes undesirable stickiness at the time of application.

These polyethylene glycols may be blended in the amount specifically described above to dissolve ketoprofen stably in an aqueous base without using glycerin, to enhance fluidity of the paste, thereby producing the paste with excellent spread-ability. Accordingly, it is possible to form a ketoprofen lysine salt-containing aqueous patch which has a good initial adhesive power.

The base components used for the ketoprofen lysine salt-containing aqueous patch provided by the present invention are not particularly limited, as long as they are ones commonly used for the production of aqueous patches. For example, water-soluble polymers, humectants, excipients, stabilizing agents, cross-linking agents, anti-oxidizing agents, cooling agents or the like may be blended as appropriate.

Examples of water-soluble polymers include gelatin, hydrolyzed gelatin, polyacrylic acid, sodium polyacrylate, partially neutralized polyacrylic acid, polyacrylic acid-starch complexes, polyvinyl alcohol, polyvinylpyrrolidone, hydroxypropylcellulose, hydroxypropyl methylcellulose, hydroxyethyl cellulose, methylcellulose, carmellose sodium, carboxyvinyl polymer, methoxy ethylene-maleic anhydride copolymers, N-vinyl acetamide copolymers, xanthan gum, and gum arabic. They may be used singly or in a combination of two or more thereof.

The content of the water-soluble polymer in the paste composition is preferably 3 to 20% by weight, and more preferably 5 to 15% by weight. When the content is less than 3% by weight, paste viscosity becomes very low and the paste loses consistency, and therefore it is difficult to shape the patch. On the other hand, the content of more than 20% by weight is not preferable, since the water-soluble polymer is not dissolved homogeneously in the paste and good paste is not formed.

Examples of the humectant include D-sorbitol solution, pyrrolidone carboxylates and the like, with the exception of glycerin, and may be used singly or in a combination of two or more thereof. The content of the humectant is preferably 10 to 30% by weight.

Example of the excipient include kaolin, titanium oxide, silicic acid anhydride, zinc oxide, bentonite and the like, and may be used singly or in a combination of two or more thereof.

Examples of the stabilizing agent include edetates, tartaric acid, citric acid, sodium hydrogensulfite and the like, and may be used singly or in a combination of two or more thereof.

The pH of the paste composition is preferably in the range of from pH 3.5 to 6.5, and more preferably in the range of from pH 4.0 to 5.5 in terms of skin irritation.

Examples of the cross-linking agent include polyvalent metal compounds such as dried aluminum hydroxide gel, synthetic aluminum silicate, dihydroxy aluminum aminoacetate, synthetic hydrotalcite, magnesium aluminometasilicate, magnesium aluminosilicate and the like, and may be used singly or in a combination of two or more thereof. Although the content thereof varies between different cross-linking agents, the preferable content is 0.001 to 1% by weight.

Examples of the anti-oxidizing agent include tocopherol acetate, ascorbic acid, butylated hydroxytoluene, tocopherol and the like, and may be used singly or in a combination of two or more thereof.

Examples of the cooling agents include 1-menthol derivatives such as camphor, thymol, 1-menthol, N-ethyl-p-menthane-carboxamide, p-menthane-3,8-diol, 1-isopulegol, 1-menthyl glyceryl ether and the like, and they may be used singly or in a combination of two or more thereof as appropriate. Furthermore, preservatives, plasticizing agents, emulsifiers, surfactants and the like may be blended if necessary.

The thickness of the paste in the aqueous patch provided by the present invention is preferably 250 to 1400 μm, and more preferably 300 to 1000 μm. When the thickness of the paste is less than 250 μm, continuous stickiness or adhesiveness tends to decrease. On the other hand, when the thickness of the paste is more than 1400 μm, cohesion or shape retention tends to decrease.

Examples of the plastic film to cover the surface of the paste composition include polyethylene, polypropylene, polyester, polyvinyl chloride, release paper and the like, and may be used singly or in a laminated form. Furthermore, such materials whose surfaces underwent silicone treatment, corona discharge treatment, embossing, plasma treatment or the like may also be used.

On the other hand, examples of a backing layer for the aqueous patch include porous materials such as polyethylene, polypropylene, polyvinyl chloride, polyester, nylon, polyurethane, and rayon, and foams, woven fabrics, nonwoven fabrics, as well as laminated materials of films or sheets and porous materials, foams, woven fabrics, or nonwoven fabrics and the like.

The method for producing an aqueous patch provided by the present invention is not particularly limited, and the aqueous patch can be produced with any known production method. For example, a ketoprofen lysine salt-containing aqueous patch can be formed by spreading the paste composition constituted of the composition as described above onto a backing layer and covering the surface of the paste composition with a plastic film.

EXAMPLES

Hereinafter, the present invention will be described more specifically with reference to Examples and Comparative Examples, but the present invention is not limited thereto.

Example 1

A patch of Example 1 was produced based on the composition of paste of Example 1 shown in Table 1 below in accordance with the following procedures.

0.5 g of hydroxypropylcellulose, 0.15 g of methyl paraben, 0.06 g of sodium edetate, 0.06 g of dihydroxy aluminum aminoacetate, 0.5 g of tartaric acid, 4.5 g of carmellose sodium, 20 g of 20% polyacrylic acid aqueous solution, 4 g of partially neutralized polyacrylic acid, 0.2 g of Polysorbate 80, 25 g of 70% D-sorbitol solution, 15 g of Polyethylene glycol 200, 0.5 g of menthol, 0.5 g of tocopherol acetate, 0.5 g of polyvinyl alcohol, and purified water (q.s.) were mixed homogeneously to prepare a hydrogel.

Subsequently, 1.5 g of a ketoprofen lysine salt was dissolved in purified water (q.s.), and then the solution was mixed homogeneously into the previously prepared hydrogel to produce a paste for the patch. The paste was applied onto a backing layer consisting of a laminated nonwoven fabric of a polyethylene film and rayon fiber at a paste density of 300 g/m$^2$, covering the adhesive face with a polyester film, and die-cutting it into a rectangle 7 cm long and 10 cm wide, thereby producing the patch.

Examples 2 to 4 and Comparative Examples 1 to 3

Aqueous patches of Examples 2 to 4 and Comparative Examples 1 to 3 were produced based on the compositions shown in Table 1 below in accordance with similar procedures to those in Example 1.

In the aqueous patches of Comparative Examples 1 to 3, concentrated glycerin was used instead of polyethylene glycol.

Polyethylene glycol 1500 could not be blended into a patch due to the high hydrophobicity thereof.

TABLE 1

| composition of paste | Examples | | | | Comparative Examples | | |
|---|---|---|---|---|---|---|---|
| | 1 | 2 | 3 | 4 | 1 | 2 | 3 |
| | (% by weight) | | | | | | |
| ketoprofen lysine salt | 1.5 | 1.5 | 1.5 | 1.5 | 1.5 | 1.5 | 1.5 |
| hydroxypropyl-cellulose | 0.5 | 0.5 | 0.5 | 0.5 | 0.5 | 0.5 | — |
| methylparaben | 0.15 | 0.15 | 0.15 | 0.15 | 0.15 | 0.15 | 0.15 |
| sodium edetate | 0.06 | 0.06 | 0.06 | 0.06 | 0.06 | 0.06 | 0.10 |
| Dihydroxy aluminum aminoacetate | 0.06 | 0.06 | 0.06 | 0.06 | 0.06 | 0.06 | 0.07 |
| tartaric acid | 0.5 | 0.5 | 0.5 | 0.5 | 0.5 | 0.5 | 1.2 |
| carmellose sodium | 4.5 | 4.5 | 4.5 | 4.5 | 4.5 | 4.5 | 3.0 |
| 20% polyacrylic acid aqueous solution | 20 | 20 | 20 | 20 | 20 | 20 | — |
| Partially neutralized polyacrylic acid | 4 | 4 | 4 | 4 | 4 | 4 | 5 |
| Kaolin | — | — | — | — | — | — | 3 |
| surface active agent | 0.2 | 0.2 | 0.2 | 0.2 | 0.2 | 0.2 | 0.3 |
| 70% D-sorbitol solution | 25 | 25 | 25 | 25 | — | — | 20 |
| concentrated glycerin | — | — | — | — | 25 | 35 | 20 |
| Polyethylene glycol 200 | 15 | — | — | — | 15 | — | 4 |
| Polyethylene glycol 300 | — | — | — | 7.5 | — | — | — |
| Polyethylene glycol 400 | — | 15 | — | — | — | — | — |
| Polyethylene glycol 600 | — | — | — | 7.5 | — | — | — |
| Polyethylene glycol 1000 | — | — | 15 | — | — | — | — |
| Menthol | 0.5 | 0.5 | 0.5 | 0.5 | 0.5 | 0.5 | 0.5 |
| tocopherol acetate | 0.5 | 0.5 | 0.5 | 0.5 | 0.5 | 0.5 | — |
| Polyvinyl alcohol | 0.5 | 0.5 | 0.5 | 0.5 | 0.5 | 0.5 | 2.75 |
| purified water | q.s. | q.s. | q.s. | q.s. | q.s. | q.s. | q.s. |
| backing layer | laminated nonwoven fabric of a polyethylene film and rayon fiber | | | | | | |
| liner | polyester film | | | | | | |

Experimental Example 1

The patches of respective Examples 1 to 4 and Comparative Examples 1 to 3 as described above were sealed in aluminum bags so that each bag includes 5 patches from each example. The bags were stored for one month at 40° C. or 50° C. The ketoprofen content in each formulation after storage and the ratio of ketoprofen glycerin ester, being a degradation product, to ketoprofen were determined by high performance liquid chromatography.

The results obtained are shown in Table 2 and Table 3 below.

Table 2: The Percentage of Ketoprofen Remaining in Each Formulation Relative to the Initial Amount

TABLE 2

| | Initial amount | 40° C./ one month | 50° C./ one month |
|---|---|---|---|
| Example 1 | 100 | 98.2 | 97.5 |
| Example 2 | 100 | 100.5 | 99.5 |
| Example 3 | 100 | 98.2 | 99.5 |
| Example 4 | 100 | 100.6 | 99.0 |
| Comparative Example 1 | 100 | 97.4 | 96.6 |
| Comparative Example 2 | 100 | 97.0 | 92.2 |
| Comparative Example 3 | 100 | 98.3 | 96.8 |

Table 3: The Percentage of Ketoprofen Glycerin Ester, being a Degradation Product, in Each Formulation

TABLE 3

| | Initial amount | 40° C./ one month | 50° C./ one month |
|---|---|---|---|
| Example 1 | 0.0 | 0.0 | 0.0 |
| Example 2 | 0.0 | 0.0 | 0.0 |
| Example 3 | 0.0 | 0.0 | 0.0 |
| Example 4 | 0.0 | 0.9 | 0.0 |
| Comparative Example 1 | 0.2 | 1.2 | 2.4 |
| Comparative Example 2 | 0.2 | 1.5 | 4.1 |
| Comparative Example 3 | 0.1 | 0.7 | 1.4 |

As is clear from the results shown in Table 2 and Table 3, the aqueous patches of the present invention utilizing polyethylene glycol (Examples 1 to 4) showed significantly better storage stability under severe conditions as compared to the patches using glycerin (Comparative Examples 1 to 3).

Comparative Example 4

With reference to Example 2 described in Japanese Patent Application Laid-Open No. 2002-193793 (Patent Document 5), a patch was produced based on the composition shown in Table 4 in accordance with similar procedures to those in Example 1 so that the ketoprofen content per unit area was 30 mg/140 cm$^2$ (equivalent to 47 mg/140 cm$^2$ of a ketoprofen lysine salt).

Comparative Example 5

A commercially available aqueous patch which contained 0.3% by weight of ketoprofen as an active ingredient and had a coating weight of 714 g/m$^2$ was used.

Examples 5 and 6

As with Comparative Examples 4 and 5, the pastes for Examples 5 and 6 were produced based on the compositions shown in Table 4 in accordance with similar procedures to those in Example 1 so that the ketoprofen content per unit area was 30 mg/140 cm$^2$ (equivalent to 47 mg/140 cm$^2$ of a ketoprofen lysine salt), and patches of respective Examples were produced by applying the paste onto a backing layer consisting of a laminated nonwoven fabric of a polyethylene film and rayon fiber, covering the adhesive face with a polyester film, and die-cutting it into a rectangle 10 cm long and 14 cm wide.

TABLE 4

| | Examples | | Comparative Example |
|---|---|---|---|
| | 5 | 6 | 4 |
| components of paste | (% by weight) | | |
| ketoprofen lysine salt | 1.12 | 0.47 | 0.47 |
| hydroxypropylcellulose | 0.5 | 0.5 | — |
| methylparaben | 0.15 | 0.15 | 0.15 |
| sodium edetate | 0.06 | 0.06 | 0.10 |
| dihydroxy aluminum aminoacetate | 0.06 | 0.06 | 0.07 |
| tartaric acid | 0.5 | 0.5 | 1.2 |
| carmellose sodium | 4 | 4 | 3.0 |
| 20% polyacrylic acid aqueous solution | 20 | 20 | — |
| partially neutralized polyacrylic acid | 4 | 4 | 5 |
| kaolin | — | — | 3 |
| surface active agent | 0.2 | 0.2 | 0.3 |
| 70% D-sorbitol solution | 25 | 25 | 20 |

TABLE 4-continued

|  | Examples | | Comparative Example |
|---|---|---|---|
| | 5 | 6 | 4 |
| components of paste | (% by weight) | | |
| concentrated glycerin | — | — | 20 |
| Polyethylene glycol 200 | — | — | 4 |
| Polyethylene glycol 300 | — | — | — |
| Polyethylene glycol 400 | 15 | 15 | — |
| Polyethylene glycol 600 | — | — | — |
| Polyethylene glycol 1000 | — | — | — |
| menthol | 0.5 | 0.5 | 0.5 |
| tocopherol acetate | 0.5 | 0.5 | — |
| polyvinyl alcohol | 0.5 | 0.5 | 2.75 |
| purified water | q.s. | q.s. | q.s. |
| coating weight | 300 | 714 | 714 |
| backing layer | laminated nonwoven fabric of a polyethylene film and rayon fiber | | |
| liner | polyester film | | |

Experimental Example 2

Skin was excised from the abdomen of a Wistar rat (6 to 7 week old) and mounted onto a Franz diffusion cell. The patches of Examples 5 and 6 and Comparative Examples 4 and 5 were die-cut into round test pieces with 16 mm in diameter (each containing 0.43 mg of ketoprofen), and the test pieces were applied onto the top of the rat skin in the diffusion cell.

Phosphate buffered saline was used as a receptor fluid, and the amount of drug that permeated the rat skin was determined by sampling the receptor fluid periodically and measuring the concentration of ketoprofen in the collected samples by HPLC.

The test result is shown in FIG. 1.

As is understood from the result, the aqueous patches of Examples 5 and 6 showed more drug permeation and good sustained drug release which was equal or longer as compared to the commercially available cataplasm of Comparative Example 5.

INDUSTRIAL APPLICABILITY

As described above, the present invention provides an aqueous patch which is produced with a simpler manufacturing operation and includes a ketoprofen lysine salt stably by employing a highly water-soluble ketoprofen lysine salt as an active ingredient and dissolving the salt in a paste including not glycerin but a polyethylene glycol having an average molecular weight of 1000 or less.

The aqueous patch provided by the present invention has both excellent transdermal absorption and storage stability of ketoprofen, which conventional aqueous patches including ketoprofen in a dissolved or dispersed form had not successfully had, and thus, it has great medical benefit.

The invention claimed is:

1. A ketoprofen lysine salt-containing aqueous patch comprising a paste, wherein the paste consists essentially of a ketoprofen lysine salt, a solubilizer, a humectant, a polyvalent metal compound, water and
one or more of an aqueous polymer selected from the group consisting of polyacrylic acid, sodium polyacrylate, partially neutralized polyacrylic acid, polyacrylic acid-starch complexes, polyvinyl alcohol, hydroxypropylcellulose, hydroxypropyl methylcellulose, hydroxyethyl cellulose methylcellulose, carmellose sodium, carboxyvinyl polymer, methoxy ethylene-maleic anhydride copolymers, and N-vinyl acetamide copolymers,
wherein the solubilizer is a polyethylene glycol in an amount of 15 to 20% by weight of the paste having an average molecular weight of 1000 or less and the ketoprofen lysine salt is dissolved in the paste,
wherein the water is 30 to 80% by weight of the paste, and
wherein the paste does not contain glycerin.

2. The ketoprofen lysine salt-containing aqueous patch according to claim 1, wherein the polyethylene glycol is selected from the group consisting of Polyethylene glycol 200, Polyethylene glycol 400, Polyethylene glycol 600, Polyethylene glycol 1000, and mixtures thereof.

3. The ketoprofen lysine salt-containing aqueous patch according to claim 1, wherein the ketoprofen lysine salt is contained in an amount of 0.1 to 5% by weight of the paste as an active ingredient, and
wherein the one or more aqueous polymer(s) is 3 to 20% by weight of the paste, the humectants is 10 to 30% by weight of the paste, and the polyvalent metal compound is 0.001 to 1% by weight of the paste, and
wherein the paste does not contain glycerin.

4. The ketoprofen lysine salt-containing aqueous patch according to claim 2, wherein the ketoprofen lysine salt is contained in an amount of 0.1 to 5% by weight as an active ingredient, and
wherein the paste includes as paste components 3 to 20% by weight of the one or more aqueous polymer(s), 10 to 30% by weight of a humectant, and 0.001 to 1% by weight of a polyvalent metal compound, and
wherein the paste does not contain glycerin.

* * * * *